US009282926B2

(12) United States Patent
Schwotzer et al.

(10) Patent No.: US 9,282,926 B2
(45) Date of Patent: Mar. 15, 2016

(54) CAMERA FOR RECORDING SURFACE STRUCTURES, SUCH AS FOR DENTAL PURPOSES

(75) Inventors: Axel Schwotzer, Gross-Gerau (DE); Volker Schmidt, Berlin (DE)

(73) Assignee: SIRONA DENTAL SYSTEMS GMBH, Bensheim (DE)

( * ) Notice: Subject to any disclaimer, the term of this patent is extended or adjusted under 35 U.S.C. 154(b) by 1070 days.

(21) Appl. No.: 12/338,564

(22) Filed: Dec. 18, 2008

(65) Prior Publication Data

US 2010/0157019 A1    Jun. 24, 2010

(51) Int. Cl.
| | |
|---|---|
| *H04N 13/02* | (2006.01) |
| *A61B 5/00* | (2006.01) |
| *A61B 1/24* | (2006.01) |
| *A61B 1/00* | (2006.01) |
| *A61B 1/06* | (2006.01) |

(52) U.S. Cl.
CPC ........... *A61B 5/4547* (2013.01); *A61B 1/00193* (2013.01); *A61B 1/0646* (2013.01); *A61B 1/0669* (2013.01); *A61B 1/24* (2013.01); *A61B 5/0084* (2013.01)

(58) Field of Classification Search
CPC .......... A61B 6/14; A61B 5/4547; A61B 1/24; A61B 5/0084; A61B 1/00193; A61B 1/0646; A61B 1/0669; G03B 9/12; H04N 13/02
USPC ........................................................... 348/46
See application file for complete search history.

(56) References Cited

U.S. PATENT DOCUMENTS

| | | | |
|---|---|---|---|
| 3,287,562 A | 11/1966 | Connors, Jr. et al. | |
| 4,575,805 A | 3/1986 | Moermann et al. | ........... 364/474 |

(Continued)

FOREIGN PATENT DOCUMENTS

| | | |
|---|---|---|
| DE | 102005043402 A1 | 3/2007 |
| EP | 0 250 993 | 1/1988 |

(Continued)

OTHER PUBLICATIONS

International Search Report and Written Opinion of the International Searching Authority issued in the corresponding application No. PCT/EP2009/067516 dated Apr. 29, 2010.

(Continued)

*Primary Examiner* — June Sison
*Assistant Examiner* — Steven Nguyen
(74) *Attorney, Agent, or Firm* — Fitzpatrick, Cella, Harper & Scinto (57) ABSTRACT

A 3-D camera for obtaining an image of at least one surface of at least one object. The camera comprises a light source, arranged to illuminate the object, wherein a light beam emitted from the light source defines a projection optical path. The camera also includes at least one first aperture having a first predetermined size, interposed in the projection optical path such that the light beam passes through it. An image sensor receives light back-scattered by the object, the back-scattered light defining an observation optical path. At least one second aperture having a second predetermined size, is interposed in the observation optical path such that the back-scattered light passes through it. In one example embodiment of the invention, the first predetermined size is greater than the second predetermined size, and at least one optic is arranged in both the projection and observation optical paths.

22 Claims, 6 Drawing Sheets

(56) References Cited

U.S. PATENT DOCUMENTS

| | | | |
|---|---|---|---|
| 4,837,732 A * | 6/1989 | Brandestini et al. | 433/29 |
| 5,175,601 A | 12/1992 | Fitts | |
| 5,579,361 A * | 11/1996 | Augais et al. | 378/38 |
| 5,635,728 A | 6/1997 | Cantu et al. | 250/584 |
| 6,040,910 A | 3/2000 | Wu et al. | |
| 6,885,464 B1 | 4/2005 | Pfeiffer et al. | 356/602 |
| 7,050,043 B2 * | 5/2006 | Huang et al. | 345/166 |
| 2002/0085273 A1 | 7/2002 | Ito | 359/369 |
| 2004/0151369 A1 | 8/2004 | Schwotzer | 382/154 |
| 2005/0151939 A1 * | 7/2005 | English et al. | 353/97 |
| 2007/0115484 A1 | 5/2007 | Huang et al. | |
| 2007/0188769 A1 * | 8/2007 | Rohaly et al. | 356/602 |
| 2008/0094631 A1 * | 4/2008 | Jung et al. | 356/419 |
| 2008/0239140 A1 * | 10/2008 | Vinogradov | 348/347 |
| 2008/0239288 A1 | 10/2008 | Lee et al. | |
| 2009/0070068 A1 * | 3/2009 | Aso et al. | 702/167 |
| 2009/0080068 A1 * | 3/2009 | Ozawa | 359/362 |
| 2009/0153159 A1 * | 6/2009 | Reed et al. | 324/754 |
| 2009/0181346 A1 | 7/2009 | Orth | |
| 2009/0263115 A1 | 10/2009 | Suzuki et al. | 396/18 |
| 2010/0008543 A1 * | 1/2010 | Yamada | 382/106 |
| 2010/0053316 A1 * | 3/2010 | Suzuki et al. | 348/78 |
| 2010/0157019 A1 | 6/2010 | Schwotzer et al. | |
| 2010/0158490 A1 | 6/2010 | Pfeiffer et al. | |
| 2010/0284589 A1 | 11/2010 | Thiel et al. | |
| 2010/0318175 A1 * | 12/2010 | Abarca et al. | 623/1.13 |
| 2011/0311105 A1 | 12/2011 | Schwotzer et al. | |

FOREIGN PATENT DOCUMENTS

| | | |
|---|---|---|
| EP | 0 968 687 A2 | 1/2000 |
| EP | 0 987 542 A2 | 3/2000 |
| EP | 1 908 399 A1 | 4/2008 |
| JP | 2002-090650 | 3/2002 |
| JP | 2002-090650 A | 3/2002 |

OTHER PUBLICATIONS

J. Pfeiffer et al., "Dreidimensionale Optische Vermessung von Zähnen," Technisches Messen: Sensoren, Geräte, Systeme [Meterology: Sensors, Devices, Systems], pp. 254-261 (1996).

European Patent Office, International Preliminary Report on Patentability in connection with International Application No. PCT/EP2009/067861, completed Apr. 6, 2011, 11 pages (and English translation thereof).

European Patent Office, International Search Report and Written Opinion of the International Searching Authority issued in connection with International Application No. PCT/EP2009/067516, dated Apr. 29, 2010, 14 pages.

* cited by examiner

CAMERA FOR RECORDING SURFACE STRUCTURES, SUCH AS FOR DENTAL PURPOSES

BACKGROUND OF THE INVENTION

1. Field of the Invention

Example aspects of the present invention generally relate to a camera for recording surface structures on an object of interest, such as for dental purposes.

2. Related Art

3-D cameras (i.e., cameras for recording three-dimensional structures) for dental applications mostly serve the purpose of recording the surface structure of a tooth in the mouth of a patient. Therefore, they typically fulfill several requirements such as the possibility of using the camera "endoscopically" in the mouth of the patient, the possibility of placing the camera in the mouth manually, and a measuring time short enough to avoid blurring even if the camera is used without further fixation. It should further be possible to record the complete surface structure if possible in a single exposure, at a maximum in two exposures. It can be useful that the results of the measurement are displayed to the operator as shortly as possible after the exposure in order to give him the opportunity to repeat the exposure if necessary. From the resulting 3-D contour data of the surface structure a dental implant can be constructed and produced. The precision of the measurement therefore can correspond to the desired precision of the dental implant.

U.S. Pat. No. 4,575,805 discloses a 3-D camera with which a surface structure on an object of interest can be recorded in terms of height or depth differences. This conventional 3-D camera has a projection optical path and an observation optical path, which make an angle with an optical axis of the 3-D camera (the camera has two optical axes for both paths and an angle between both paths). A light source for emitting a group of light beams in the direction of an object of interest is arranged in the projection optical path. The light back-scattered by the object of interest is guided through the observation optical path to an image sensor of the 3-D camera. The signals from the image sensor can be fed to an evaluation unit, so that an image of the surface structure can be created on a display device. This 3-D camera is suitable in particular for recording a cavity of a tooth.

EP-A-0 250 993 also discloses such a 3-D camera. For determining the height or depth differences of the surface structure, means are provided for producing a reference pattern in such a way that the reference pattern can be projected onto the surface structure. With the aid of the light which is back-scattered by the surface structure and is incident on the image sensor, and in conjunction with evaluation electronics for carrying out a process which is referred to as phase-shifting triangulation and is explained in more detail in the aforementioned document, the surface structure can be assessed in terms of height and depth differences and presented as a pseudo-three-dimensional image on a monitor.

A 3-D camera is also disclosed in the journal "Technisches Messen: Sensoren, Gerate, Systeme" [Metrology: sensors, devices, systems], Jun. 1996, pages 254 to 261, Oldenbourg-Verlag B3020.

In triangulation, an object is observed by a camera with a planar detector element, which generates a two-dimensional digital image. The object is thus described by a data set in which discrete intensity values are assigned to discrete pixels in the lateral dimension. In order to generate information about the third dimension (object height z), the object is illuminated with incident light in a structured fashion and observed from a direction different from the direction of the incident light, i.e., under a triangulation angle.

The projection and the observation optics are arranged in a fixed and known spatial relationship to one another. They may be formed by the same system of lenses which are transmitted in different areas or under different angles. For influencing the beam geometry, an additional field lens may be present close to the object.

The application of phase-shifting triangulation to recording dental structures is characterized by a number of demands. For example, some are imposed by the size and typical shape of the object and by the necessary precision. For measuring edges with height differences of up to about 15 millimeters (mm) with a precision of 25 µm in all dimensions, a high lateral resolution of the optical components can be useful. The simultaneous need for a high depth of field imposes demands to the system that are at the edge of what is possible with visible light because of the diffraction limit. A short wavelength would be desirable if suitable light sources were available.

The demand of recording cavities with steep walls on all sides requires a small triangulation angle. The small object size allows to use a telecentric beam path, which leads to simplifications in the evaluation algorithms. A telecentric beam path also is a good compromise with respect to the shape to be measured, as it allows measuring cavities as well as stumps with steep flanges.

There are several techniques by which the actual measurement may be performed with a 3-D camera. Some of these are described in the above-mentioned U.S. Pat. No. 4,575,805 and the article in journal "Technisches Messen: Sensoren, Gerate, Systeme", as well as in U.S. Pat. 6,885,464, each of which is incorporated by reference herein in their entireties, as if fully set forth herein.

Reduced depth of field sharpness in known 3-D cameras can lead to reduced quality of captured images of an object within certain ranges, particularly when outside of the center of the depth of field. This limitation can occur for both "live" images and non-live still images. Prior techniques have attempted to compensate for this limitation by skillful treatment of the captured images and/or by enhanced grinding machine control for forming dental structures based on the images.

SUMMARY OF THE INVENTION

The foregoing can be addressed with a camera for obtaining an image of at least one surface of at least one object, such as a dental structure, and by a method of obtaining such an image. The camera comprises a light source, arranged to illuminate the object. The light beam emitted from the light source defines a projection optical path. At least one first aperture having a first predetermined size is interposed in the projection optical path such that the light beam passes through it. An image sensor receives light back-scattered by the at least one surface, wherein the back-scattered light defines an observation optical path. At least one second aperture having a second predetermined size is interposed in the observation optical path such that the back-scattered light passes through it. According to an example aspect of the invention, the first predetermined size and the second predetermined size are different from each other, and at least one optic is arranged in both the projection and observation optical paths.

According to an example embodiment of the invention, the camera is a 3-D camera, and the first predetermined size is greater than the second predetermined size. The camera also can include a reference pattern projector arranged in the projection optical path to form an image on the at least one surface, the reference pattern projector being an optical grid having a predetermined pattern to form the image.

According to another example embodiment of the invention, one of the first and second apertures is elliptical in shape, and at least part of another one of those apertures forms at least part of a circle. In one example, the circle includes at least one side cut.

Further features and advantages of the present invention as well as the structure and operation of various embodiments of the present invention are described in detail below with reference to the accompanying drawings.

BRIEF DESCRIPTION OF THE DRAWINGS

The features and advantages of the present invention will become more apparent from the detailed description set forth below when taken in conjunction with the drawings in which like reference numbers indicate identical or functionally similar elements.

FIGS. 3A to 3C are cross sections of a camera according to an example embodiment of the invention, such as the camera apparatus of FIG. 1, wherein FIG. 3A shows the camera as viewed from a perspective looking down towards an upper surface of the cross section depicted in FIG. 3C, and FIG. 3B shows the camera as viewed from a perspective looking up towards a lower surface of the cross section depicted in FIG. 3C.

Reference numerals that are the same in different figures represent the same elements, even though a separate description may not be provided for the elements with respect to each separate figure described herein.

DETAILED DESCRIPTION

Example aspects of the present invention relate to a camera for obtaining an image of at least one surface of at least one object. In one example embodiment of the invention, the camera comprises a light source arranged to illuminate the object with a light beam provided in a projection optical path, and at least one first aperture, having a first predetermined size, and being interposed in the projection optical path such that the light beam passes through it. An image sensor receives light back-scattered by the at least one surface of the at least one object. The back-scattered light defines an observation optical path. The camera also comprises at least one second aperture, having a second predetermined size, and being interposed in the observation optical path such that the back-scattered light passes through it. According to an example aspect of the invention, the first aperture is greater in size than the second aperture.

The use of both a projection optical path and an observation optical path in a single optical camera is characterized by competing demands. First of all, in many applications, such as those in which, for example, the camera is used for dental purposes, it is desired that the size of the overall camera be as small as possible. However, the size reduction can be limited by the size and number of optical components employed in the two paths. Accordingly, such a limitation can be overcome by employing, in each separate path, at least some shared optical elements, such as apertures and other elements. Unfortunately, however, in some applications, such as, for example, dental applications in which a diffuse pattern originating from a grating (see, e.g., the grating pattern of FIG. 6) is projected by the projection optical path onto an object of interest (e.g., a dental structure such as a tooth), the back-scattered light pattern received back from the structure into the observation optical path can be somewhat different owing to sine wave modulation, distortion, and the like. Also, cones of the dispersed, back-scattered light typically can have a large back-scatter angle, and, as a result, only a small portion of the back-scattered light gets captured for use in the observation optical path. To compensate for this, the observation optical path preferably should be designed so that there is high image sharpness (e.g., a resolution on the order of 15 to 20 microns).

The image projected onto the object of interest, on the other hand, does not necessarily need to be especially sharp. In phase-shifting triangulation, a sharp (although not especially sharp) image is needed in only one direction, and it is best that the projection path illuminate the object with as much light as would enable the image sensor to have a desired signal-to-noise ratio. However, this factor is tempered in cases where there is only a short depth of field owing to use of a large aperture, or where reflections from the projection path affect the observation path, because such situations can cause an undesirable reduction in sharpness and the depth of field in the observation path. Unfortunately, the use of apertures with similar size and shape as in the previous art for 3D-cameras with shared field lenses for the projection path and the observation path does not balance these competing demands adequately, and thus image quality suffers as a result.

The inventors have discovered that these limitations can be overcome by providing apertures with different size and shape in the projection and observation optical paths.

For example, the inventors have recognized that a sufficient amount of light can be obtained in the observation path if a large aperture is employed in the observation path. However, the inventors also have discovered that if the size of the aperture in the projection path is made larger still, enough light still can be provided in the observation path so that the aperture in the observation path can be reduced in proportion to the amount of increase in the projection path's aperture size, so that undesirable issues relating to higher sharpness in the observation path can be avoided.

Figure 6:
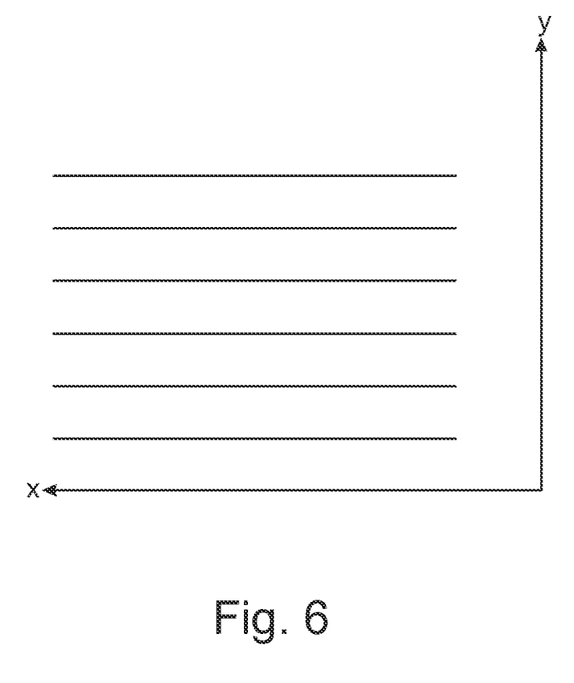
FIG. 6 shows an example grid pattern of a grid that may be employed in the camera apparatus of FIG. 2 and/or FIG. 4.

The use of a larger aperture in the projection optical path and a relatively smaller aperture in the observation optical path, enables an image of a grid pattern (such as, e.g., that of FIG. 6) to be projected onto the object of interest with good contrast along the direction represented by the y-axis in FIG. 6, and enables the version of the image pattern back-scattered by the object to have good contrast in both that same direction and in the direction represented by the x-axis in FIG. 6.

Over the dispersion of back-scattered light the intensity in each angle of incidence contributes to the intensity in each loss angle, and an asymmetrical aperture (e.g., elliptical and/or round with side-cuts) in one of the projection and observation optical paths (such as the projection path, for example) can suitably accommodate such a condition. Use of such an asymmetrical aperture in that path, in conjunction with use of a symmetrical aperture in the other of those paths, enables good energy balance to be provided in the paths. Additionally, use of a smaller aperture for receiving light rays in the observation optical path increases the depth sharpness of the image.

Accordingly, in one example embodiment of the invention, as described above, the aperture in the projection optical path is larger than the aperture in the observation optical path. By virtue of such an arrangement, the above-described competing demands can be better balanced while still enabling the image sensor to obtain a high image quality, all in a small sized optical camera.

An example embodiment of the invention will now be described in detail with reference to FIGS. 1, 2, and 3A-3C. A projection optical path 1 is defined by light beams which can be produced by an optical source 3. For example, the optical source 3 can include an infrared LED (or other light source). The projection optical path 1 can be represented by a centroid beam, which, in one example embodiment, is a beam that forms an average in relation to the cross-sectional area and intensity of the group of light beams. In this example, the position of the centroid beam in a cross-sectional surface of the group of light beams is obtained by averaging the cross-sectional point coordinates weighted with the respective light intensity at a cross-sectional point. In a group of light beams with uniform intensity and circular form, for example, the centroid beam passes through the centre of the circle.

The light beams emitted by the optical source 3 propagate in path 1 through a collimator 4 having plural lenses 4a to 4d that are, in one example, aspherical. These components are arranged and configured so that the collimator 4 collects as much light as possible from the optical source 3, collimates the light, and forwards the collimated light to a reference pattern projector, such as an optical grid 5, having a predetermined pattern (such as that shown in, e.g., FIG. 6) to be projected onto an object of interest 14 to be measured, such as, for example, one or more dental structures (e.g., actual or prosthetic teeth, dental molds, casting, etc.). In one example embodiment of the invention, the grid 5 includes a glass plate having a metal grid, although in other embodiments it may have other suitable configurations and materials depending on applicable operating criteria. Also, in one example embodiment of the invention, the grid 5 is arranged so as to face substantially perpendicularly to the beams of light received from the collimator 4. In such a manner, the intensity of light provided to the grid 5 is substantially the same over the grid 5's receiving face. The grid 5 is also is arranged in the path 1 in such a way that an image of the grid's pattern is projected onto a surface of the object 14, as will be described below.

Light beams emerging from the grid 5 are received by an objective 6, which, in the illustrated example embodiment, includes adjacent spherical lenses 6a and 6b that are arranged and configured to direct the received beams to an optical block or tube 7. The block 7 includes glass and may form a prism according to one example embodiment of the invention, although in other embodiments it may comprise other suitable materials. Also, according to an example embodiment of the invention, the block 7 can be a polarizing element (e.g., 90 degree polarization) that substantially prevents light from path 1 from interfering with or entering path 2, and vice versa. In other examples, block 7 can be a non-polarizing element, depending on applicable design criteria.

Figure 5A:
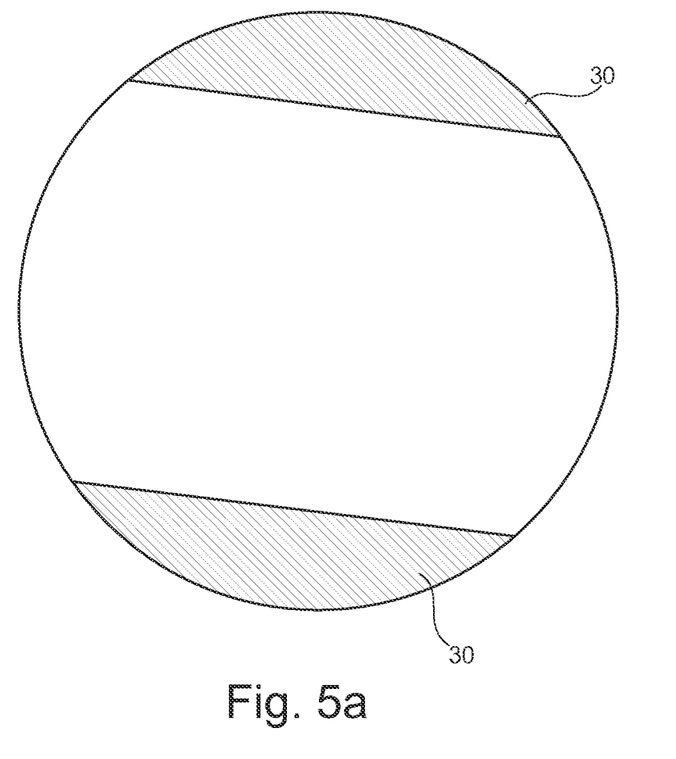
FIG. 5a depicts a cross-section of an example aperture having side cuts.
Figure 5B:
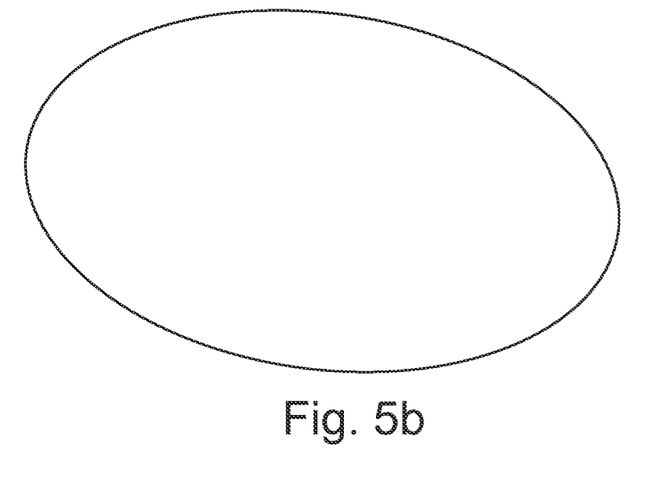
FIG. 5b depicts a cross-section of an example elliptical aperture.

According to an aspect of the invention, the optical block 7 directs light beams received in the optical path 1 towards an objective 8 which, in the illustrated example embodiment, includes adjacent spherical lenses 8a and 8b that are arranged and configured to direct the received beams to an aperture 9a formed by an aperture component 9 such as an aperture stop, for example. According to one example embodiment of the invention, the aperture 9a has a diameter that is the same as that of an emitting surface of the light source 3 multiplied by a multiplication factor (e.g., 3.5) of the collimator 4, although in other embodiments another aperture diameter can be employed. In one example, the diameter of the aperture 9a can be 2.8 mm, although of course the diameter is not limited to this specific example only. Also according to an example embodiment of the invention, the aperture 9a can be either constant in size, or can be controllably variable (using, for example, a known actuator (not shown)) so have to have a selected one of a plurality of selectable sizes. In either case, the aperture 9a can be circular in shape and have side cuts, as shown in FIG. 5a (wherein reference numeral 30 identifies cutouts representing the side cuts), can be elliptical in shape, as shown in FIG. 5b, or can have any other suitable shape (with or without side cuts), depending on applicable performance criteria, and, in one example embodiment of the invention, the aperture is controllable so as to have a selected one of plural shapes (e.g., circular, square, or any other suitable shape).

Light beams emerging from the aperture 9a in the path 1 propagate through another objective 10 which, in the illustrated example embodiment, includes adjacent lenses 10a and 10b (e.g., spherical lenses) that are arranged and configured to direct the received beams to a front lens optic 11. The lens optic 11 includes, in the illustrated example, lenses 11a and 11b that are configured and arranged to collect the received beams and provide them parallelized (for telecentricity) to a prism 12, which, in turn, deviates them at a predetermined angle with respect to the longitudinal axis of the lens optic 11 and a front face of the prism 12. The group of light beams emerging from the prism 12 strikes at least one surface 13 of the object 14 to be measured, and is back-scattered there.

The back-scattered light passes along an observation optical path (also referred to as "a reflection path") 15. The centroid beam of the observation optical path 15 intersects the surface 13, wherein an angle referred to as the triangulation angle is included between the projection optical path 1 and the observation optical path 15. The light back-scattered by the object 14 of interest is again deviated along the observation optical path 15 via the prism 12 and is delivered through the lens optic 11 and objective 10 to an aperture 9b formed by the aperture component 9. According to an example aspect of the invention, the aperture 9b in the path 15 is smaller in size (e.g., has a smaller diameter, in the case of a circular or semi-circular aperture) than the aperture 9a in the path 1. A small size for aperture 9b provides for a greater depth-of-field (DOF). In one example embodiment of the invention, the aperture 9b has a diameter of 1.6 mm, although of course the aperture size is not limited to this specific example only. Also according to an example embodiment of the invention, like the aperture 9a, the aperture 9b can have a constant size, or can be controllably variable so as to have a selected size. In either case, the aperture 9a can be circular, semi-circular, or elliptical in shape, or can have any other suitable shape, depending on applicable performance criteria, and, in one example embodiment of the invention, the aperture is controllable so as to have a selected one of plural shapes (e.g., circular, semi-circular, elliptical, square, or any other suitable shape). An example aperture shape that can be employed for aperture 9b is shown FIG. 5a, and another example is shown in FIG. 5b.

Although the apertures 9a and 9b are described above in the context of being included in a same aperture component 9, in other embodiments they can be provided in separate aperture components.

According to an example embodiment of the invention, at least part of the beam paths 1 and 15 are telecentric. As but one example, at least the portion of the camera from the objective 10 to the front lens 11 can be telecentric.

Light beams emerging from the aperture 9b in the path 15 propagate through the objective 8 to an optical block or tube 16, which in one example, comprises glass and forms a prism. The block 16 deviates the light beams it receives in at least one direction at a predetermined angle relative to the block 16's receiving face, and provides them to an image sensor 17 by way of an objective 18. In the illustrated example embodiment, the objective 18 includes adjacent lenses 18a and 18b (e.g., spherical lenses) that are arranged and configured to direct light beams received thereby to the image sensor 17.

According to an example embodiment of the invention, the image sensor 17 is a CCD having 768 pixels by 494 pixels, and can obtain images at a rate of about 30 images per second, although of course in other embodiments other types of image sensors can be employed.

The image sensor 17 converts the received light signals into electrical signals which are delivered to a signal-processing device, known from the documents cited at the start, so as to obtain data from which an image of the surface structure of the object 14 of interest can be created.

As can be appreciated in view of the above description, by providing a smaller sized aperture in the observation path 15 than in the projection path 1, a sharper image of the object 14 can be obtained by the image sensor 17 (in addition to better energy balance being provided) relative to a case where the apertures in the paths 1 and 15 have a same size, and thus, the quality of the image is better than would in such a case. As a result, higher quality dental restorations, for example, can be formed based on the obtained images.

Moreover, any reduction in the light of path 15 resulting from the use of the smaller aperture 9b, can be compensated for by using at least one of a more powerful light source 3 than would be used conventionally, and an image sensor 17 having a greater signal-to-noise ratio than would be used conventionally. Additional compensation can be provided by further increasing the size of the aperture 9a relative to the size of aperture 9b, changing the shape of at least one of those apertures, and/or employing, in the path 1, at least one additional aperture that is sized larger than the aperture 9b. While at least some of these factors may decrease the sharpness of the image projected onto the object 14 by the projection path 1, they can create greater sharpness in the observation path 15.

A grating (e.g., grating 5 and/or another grating) can be inserted into the projection optical path 1 which can be moved in a direction perpendicular to the lines of the grating by a piezo actuator (not shown), and, in one embodiment, the shapes of the apertures can be controlled by a controller (not shown), either automatically or through manual activation. In the embodiment where the grating is employed, the grating can be employed as the reference pattern projector, and is arranged in the beam in such a way that an image of the grating is projected onto the surface 13, forming a reference pattern on the surface. By activating the piezo actuator, the grating can be moved, and the reference pattern correspondingly moves across the surface 13. Alternatively, instead of a mechanical grating, an LCD element could be employed for generating a reference pattern.

Of course, other optical elements besides those depicted in the mentioned figures can also be employed, although they have not been represented for the sake of simplicity. Examples of various optical elements that can be employed are described in the aforementioned journal "Technisches Messen", pages 257, FIG. 6, and in the U.S. patents referred to above.

Figure 1:
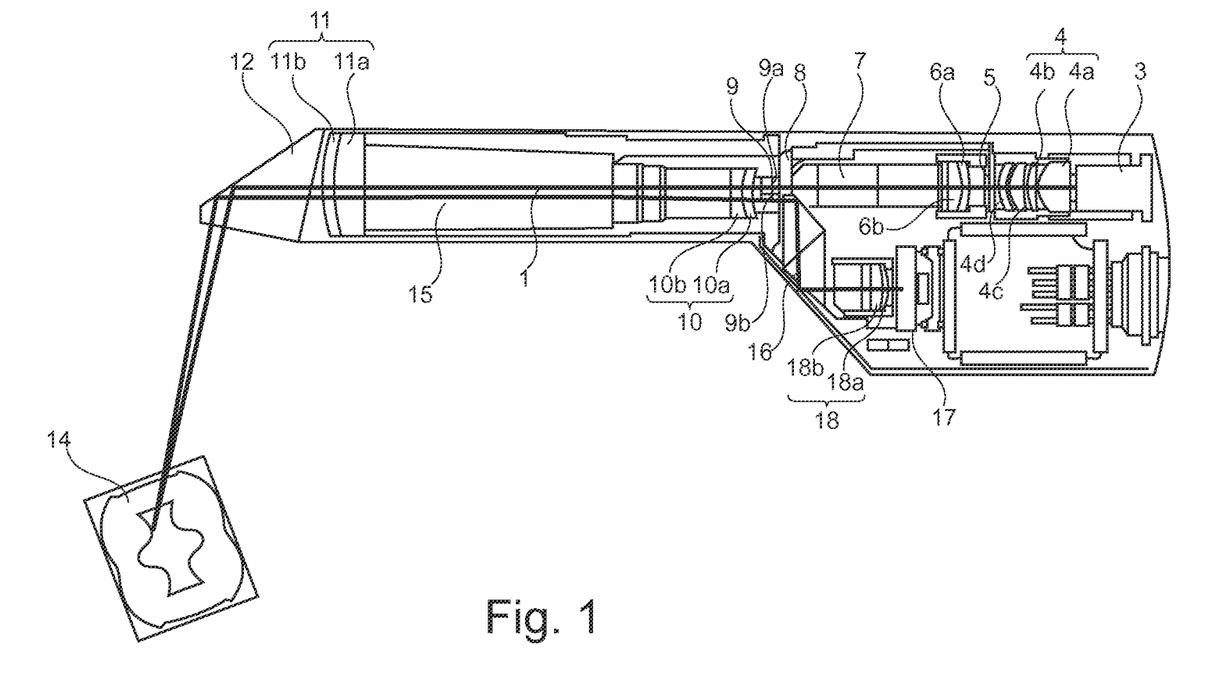
FIG. 1 is a block diagram of a camera apparatus according to an example embodiment of the invention.
Figure 2:
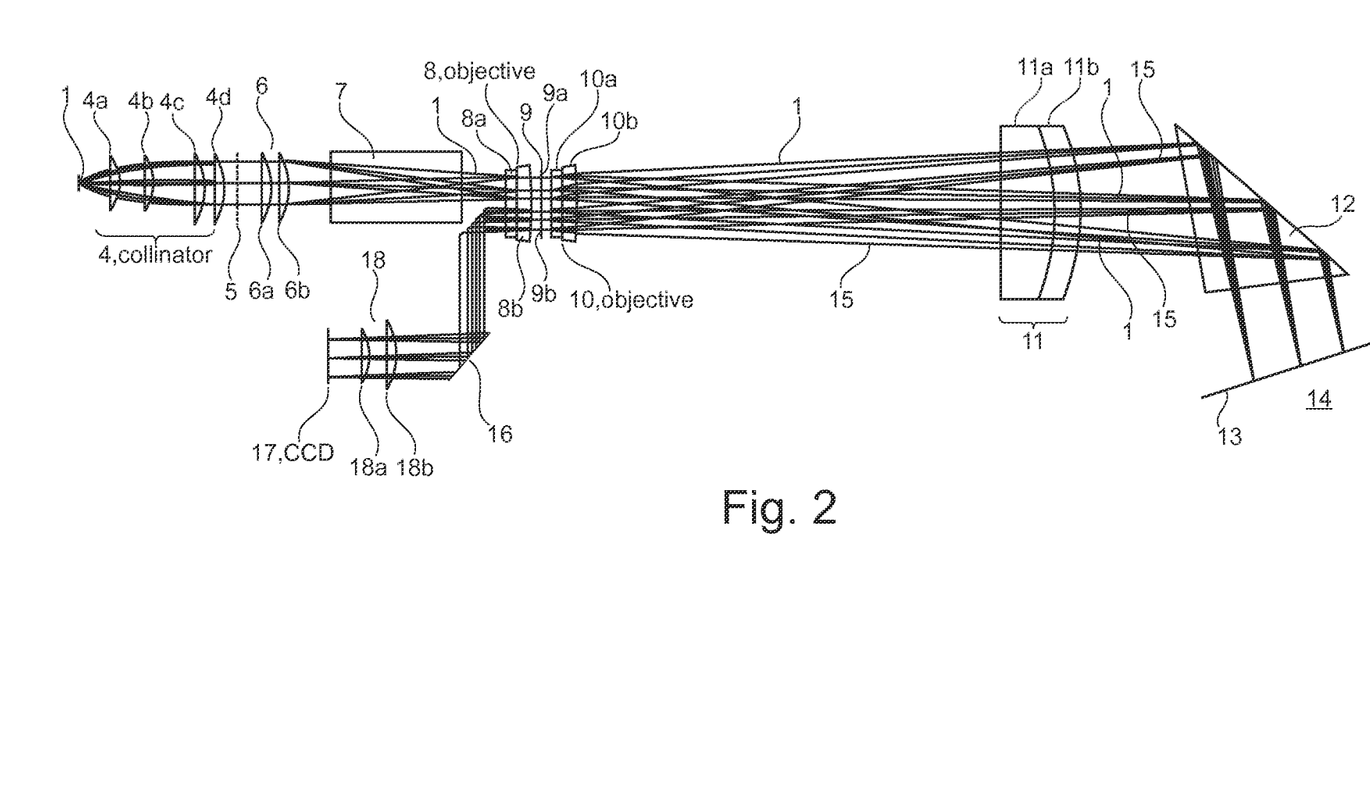
FIG. 2 is a block diagram of a projection optical path 1 and an observation optical path 15 of a camera apparatus, such as that of FIG. 1, and also depicts optical components arranged or interposed in those paths.
Figure 3A:
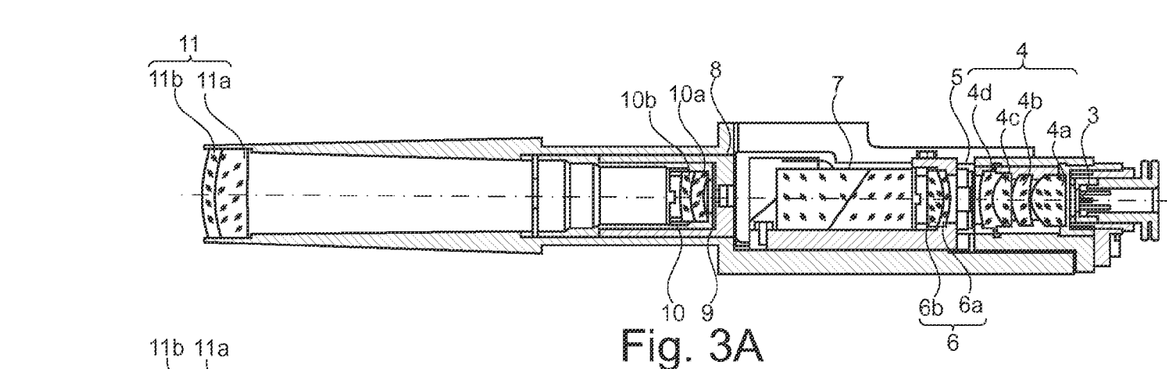
Figure 3B:
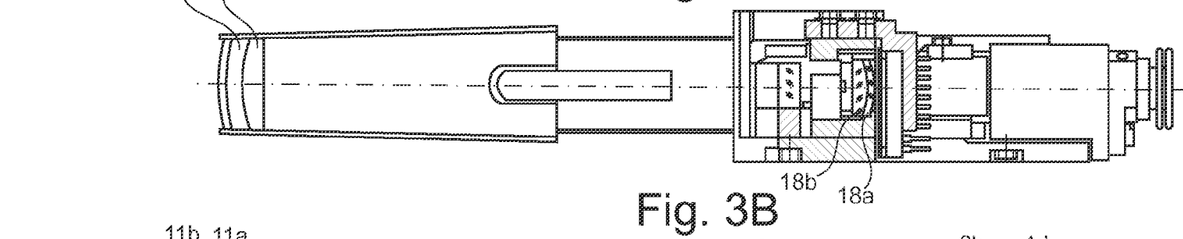
Figure 3C:
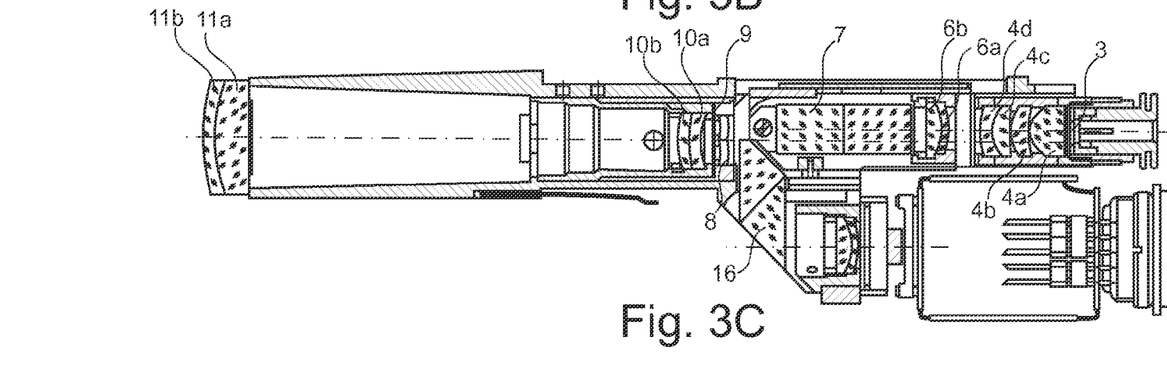
Figure 4:
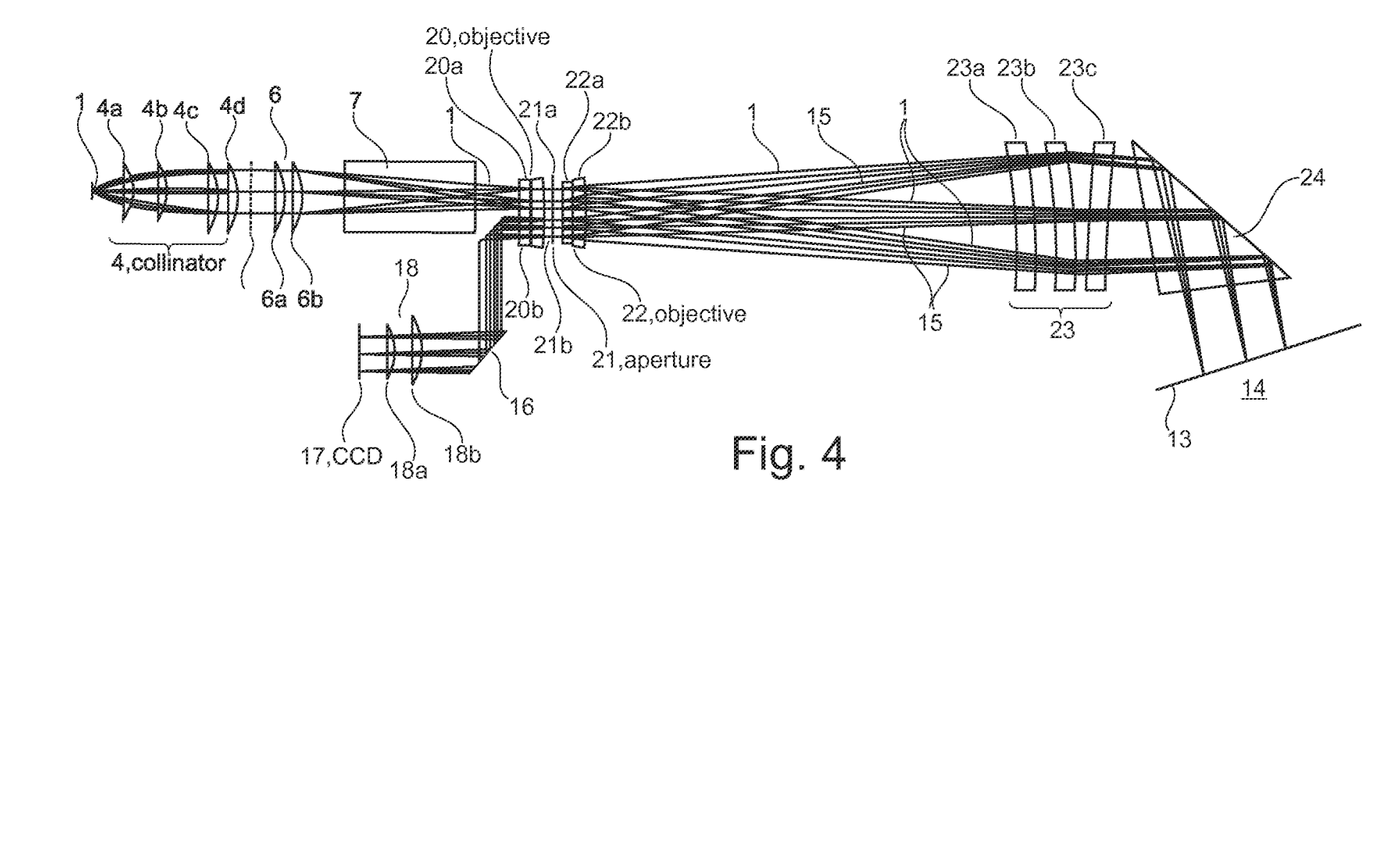
FIG. 4 is a block diagram of a projection optical path 1 and an observation optical path 15 of a camera apparatus according to another example embodiment of the invention, and also depicts optical components arranged or interposed in those paths.

According to another example embodiment of the invention, the elements shown in FIGS. 2 can have another configuration, such as, for example, that depicted in FIG. 4. FIG. 4 depicts a camera apparatus according this example embodiment of the invention, wherein the components 1, 3, 4, 5, 6, 7, 13, 14, 15, 16, 17, and 18 are the same and operate in the same manner as those same-numbered components of FIG. 2. Because those components and the manner in which they function were described above, a further description of at least some of those components will not now be provided, and the following description will begin with optical block 7.

Referring to FIG. 4, the optical block 7 directs light beams received in the optical path 1 from objective 6, towards an objective lens component 20a of an objective 20, which, in the example shown in FIG. 4, includes the lens component 20a and a lens components 20b, each of which can include one or more lenses (e.g., aspherical lenses). At least lens component 20a is arranged and configured to direct the beams received thereby to an aperture 21a formed by an aperture component 21 such as an aperture stop, for example. Also according to an example embodiment of the invention, the aperture 21a can be either constant in size and shape, or can be controllably variable so have to have a selected one of plural possible sizes and shapes. Aperture 21a can have any suitable shape (including, for example, one of those depicted in FIGS. 5a and 5b, among other shapes), depending on applicable design criteria.

Light beams emerging from the aperture 21a in the path 1 propagate through another objective 22 which, in the illustrated example embodiment, includes adjacent lenses 22a and 22b (e.g., spherical lenses), at least one of which is arranged and configured to direct the received beams to a front lens optic 23. The lens optic 23 includes, in the illustrated example, lenses 23a, 23b, and 23c that are configured and arranged to collect the received beams and provide them in a parallel manner to a prism 24. According to an example aspect of the invention, the lenses 23a, 23b, and 23c are tilted relative to one another to avoid or substantially minimize the possibility that reflections caused by one path, such as path 1, will interfere with another one of the paths, such as path 15, or the components interposed therein. Reflections in the opposite direction, on the other hand, are avoided or substantially minimized because direct reflections of light from path 1 by one of the plural (e.g., 6) surfaces of the three lenses do not reach the aperture 21b.

The prism 24 deviates light beams received thereby at a predetermined angle with respect to a receiving face of the prism 24. The group of light beams emerging from the prism 24 strikes at least one surface 13 of the object 14 to be measured, and is back-scattered there.

The back-scattered light passes along an observation optical path 15. The centroid beam of the observation optical path 15 is directed from the surface 13, such that an angle referred to as the triangulation angle is formed between the projection optical path 1 and the observation optical path 15. The light back-scattered by the object 14 of interest is again deviated along the observation optical path 15 via the prism 24 and is delivered through the lens optic 23 and objective 22 to an aperture 21b formed by aperture component 20.

According to an example aspect of the invention, the aperture 21b in the path 15 has a smaller size (e.g., diameter) than the aperture 21a in the path 1. A smaller size for aperture 21b provides for a greater depth-of-field (DOF). In one example embodiment of the invention, the aperture 21b has a diameter of 1.6 mm, and the aperture 21a has a diameter of 2.8 mm, although of course the diameters are not limited to these specific examples only. Also according to an example embodiment of the invention, the aperture 21b can have a constant size and shape (including, for example, one of the shapes depicted in FIG. 5a and 5b, among other possible shapes), or can be controllably variable so have to have a selected size and shape, as described above.

Although the apertures 21a and 21b are described above in the context of being included in a same aperture component 21, in other embodiments they can be provided in separate aperture components. Also, according to an example embodiment of the invention, at least part of the beam paths 1 and 15 in the illustrated embodiment are telecentric. For example, at least the portion of the system from the objective 22 to the front lens 23 can be telecentric.

Light beams emerging from the aperture 21b in the path 15 propagate through the objective 20 to prism 16, which in one example, deviates them at least once at a predetermined angle relative to a receiving face of the prism 16, and provides them to an image sensor 17 by way of an objective 18. Like the objective 18 of FIG. 2C, the objective 18 of FIG. 4 can include adjacent aspherical lenses 18a and 18b that are arranged and configured to direct light beams received thereby to the image sensor 17, which operates in the above-described manner.

Other components also can be provided in the paths 1 and 15 of the present embodiment, as described above for the embodiment of FIG. 2.

As can be appreciated in view of the description of the present embodiment, by providing a smaller sized aperture in the observation path 15 than in the projection path 1, a sharper image of the object 14 can be obtained by the image sensor 17 (in addition to better energy balance being provided) relative to a case where the apertures in the paths 1 and 15 have a same size, and thus the quality of the image is better than would in such a case. As a result, higher quality dental restorations, for example, can be formed based on the obtained images.

Moreover, any reduction in the light of path 15 resulting from the use of the smaller aperture 21b can be compensated for by using at least one of a more powerful light source 3 than would be used conventionally, and an image sensor 17 having a greater signal-to-noise ratio than would be used conventionally. Additional compensation can be provided by further increasing the size of the aperture 21a relative to the size of aperture 21b, changing the shape of at least one of those apertures, and/or employing, in the path 1, at least one additional aperture that is sized larger than the aperture 21b. While at least some of these factors may decrease the sharpness of the image projected onto the object 14 by the projection path 1, they can create greater sharpness in the observation path 15.

In some embodiments of the invention, one or more of the cameras described above (FIGS. 2 and 4) can employ one type of shaped aperture in the projection optical path 1, and at least one other type of shaped aperture in the observation path 15. As but one example, the aperture included in the path 1 can be elliptical (see, e.g., FIG. 5b) to provide for a better depth of field than in the path 15, in which the aperture can be circular or semi-circular (see, e.g., FIG. 5a) since a high quality depth of field in that path is not as useful for path 15 relative to path 1. Alternatively, the aperture in path 15 can be elliptical (see, e.g., FIG. 5b), and the aperture in path 1 can be circular or semi-circular (see, e.g., FIG. 5a). Also in one example embodiment of the invention, the aperture employed in the observation optical path can be rotationally symmetric and the aperture included in the projection optical path can be non-rotationally symmetric, or vice versa. Also in an example embodiment of the invention employing an the elliptical aperture, that aperture can extend along an axis that is parallel to the lines of the grid pattern (e.g., FIG. 6) received thereby.

Also in some example embodiments of the invention, in a case where one or more elliptical apertures are employed, a shorter axis of the ellipse (whether including the side-cuts or not) can be parallel to the grid lines. This feature can make the direction perpendicular to the grid lines sharper. The size of the shorter axis of an aperture can determine the sharpness (modulation transfer function (MTF)), and can be proportional to the resolution (LP/mm) of the grid, so that the contrast (MTF) of the grid in the depth of field used (e.g., depth of teeth of about 15 mm) extends by a certain value. This can determine a signal-to-noise ratio of the 3D image. In one example, the size of the longer axis of an aperture can be determined by the whole aperture size to be illuminated, and the image of the light source can be, at a minimum, that size or proportional thereto. In a case where a round- or quadratic-shaped light source is employed (which is usual in cases where LEDs are employed), and where a long-shaped aperture is employed, at least some light emitted by the light source may or may not pass through the aperture. The size of the aperture in the observation path, which can determine sharpness (MTF), can be proportional to the resolution (LP/mm) of the image sensor 17, as determined by pixel size, so that the contrast (MTF) of the image in the depth of field used (e.g., depth of teeth of about 15 mm) extends by a certain value. If the aperture is small enough that the sharpness (MTF) is determined by the image sensor in the whole depth of field, the aperture can be enlarged to provide for more light and a better signal-to-noise ratio on the image sensor. In at least some example embodiments, the sharpness of the image on the image sensor can correlate to the resolution of the equipment (e.g., milling machine and the like) used to form the object(s) (e.g., dental structure(s)) of interest, and also can correlate to the resolution of the displayed 3D images In the example embodiments described above, the objectives are described as having one or more lenses. It should be noted that the number of lenses shown and described with respect to those embodiments is not intended to be limiting, and that any suitable number of lenses can be employed, depending on applicable design criteria. Also, the embodiment of FIG. 2 and 4 can employ lenses like those of objective 8 in lieu of the lenses 20a and 20b, and vice versa, depending on applicable design criteria.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above described exemplary embodiments, but should be defined only in accordance with the following claims and their equivalents.

What is claimed is:

1. A method of obtaining an image of at least one surface of at least one object, the method comprising:

providing a light beam that projects an image through at least one first aperture onto the at least one surface of the at least one object, wherein the image is formed by a reference pattern projector that is arranged in a path of the light beam and is an optical grid having a predetermined pattern; and providing light back-scattered by the at least one surface, and representing a further version of the image projected onto the at least one surface, through at least one second aperture to an image sensor, wherein at least one of the first and second apertures is elliptical in shape and another of the first and second apertures is non-elliptical in shape, wherein an axis along which the at least one aperture that is elliptical in shape extends is perpendicular to an axis along which at least part of the predetermined pattern extends, wherein the first aperture has a predetermined size that is larger than a size of the second aperture, such that the image projected onto the object has contrast along at least one direction, and the further version of the image has contrast along at least two directions, and wherein the at least one object is a dental object.

2. A method as set forth in claim 1, wherein the method is performed by a 3-D camera.

3. A method as set forth in claim 1, further comprising:
controllably varying at least one of a size of the first aperture and the size of the second aperture.

4. A method as set forth in claim 1, wherein the light beam and back-scattered light are provided in a single camera that comprises a plurality of optics, each optic being arranged in at least one path through which the light beam and back-scattered light travel.

5. A method as set forth in claim 1, wherein the first aperture has the predetermined size that is larger than the size of the second aperture, to enable the image sensor to have a certain signal-to-noise ratio.

6. A method as set forth in claim 1, wherein the path of the light beam defines a projection optical path, and
wherein the light back-scattered by the at least one surface defines an observation optical path.

7. A method as set forth in claim 6, wherein at least one collimator is arranged in the projection optical path.

8. A method as set forth in claim 6, wherein at least one optical block is arranged in at least one of the projection optical path and the observation optical path.

9. A method as set forth in claim 8, wherein the at least one optical block is polarized.

10. A method as set forth in claim 6, wherein at least one optical lens is arranged in at least one of the projection optical path and the observation optical path.

11. A method as set forth in claim 6, wherein plural optical lenses are arranged in at least one of the projection optical path and the observation optical path, and
wherein the lenses are tilted with respect to one another.

12. A method as set forth in claim 6, wherein at least one optical prism is arranged in at least one of the projection optical path and the observation optical path.

13. A method as set forth in claim 6, wherein plural optical objectives are arranged in at least one of the projection optical path and the observation optical path, on opposite sides of the first and second apertures.

14. A method as set forth in claim 1, wherein an axis along which the at least one aperture that is elliptical in shape extends is perpendicular to an axis along which at least part of the predetermined pattern extends.

15. A method as set forth in claim 1, wherein the other of the first and second apertures is semi-circular in shape.

16. A method as set forth in claim 1, wherein one of the first and second apertures forms at least part of a circle.

17. A method as set forth in claim 16, wherein the circle has at least one side cut.

18. A method as set forth in claim 1, wherein at least one of the size of the first aperture and the size of the second aperture is controllably variable.

19. A method as set forth in claim 6, wherein at least one optic is arranged in the projection optical path and the observation optical path.

20. A method as set forth in claim 19, wherein the at least one optic is telecentric.

21. A method as set forth in claim 19, wherein the at least one optic includes at least one of an objective, a lens optic, and a prism.

22. A method as set forth in claim 19, wherein the at least one optic, the light source, the first and second apertures, and the image sensor are housed in a housing.

* * * * *

UNITED STATES PATENT AND TRADEMARK OFFICE
CERTIFICATE OF CORRECTION

PATENT NO. : 9,282,926 B2
APPLICATION NO. : 12/338564
DATED : March 15, 2016
INVENTOR(S) : Schwotzer et al.

It is certified that error appears in the above-identified patent and that said Letters Patent is hereby corrected as shown below:

In the Drawings

FIG 2:

"collinator" should read --collimator--.

FIG 4:

"collinator" should read --collimator--.

In the Specification

COLUMN 6:

Line 19, "so have to have" should read --so as to have--.

COLUMN 7:

Line 3, "shown FIG. 5a," should read --shown in FIG. 5a,--; and
Line 39, "than would" should read --than would be--.

COLUMN 8:

Line 13, "according this" should read --according to this--;
Line 26, "a lens components" should read --a lens component--; and
Line 33, "so have to have" should read --so as to have--.

Signed and Sealed this
Twenty-third Day of August, 2016

Michelle K. Lee
*Director of the United States Patent and Trademark Office*

CERTIFICATE OF CORRECTION (continued)
U.S. Pat. No. 9,282,926 B2

<u>COLUMN 9:</u>

Line 14, "so have to have" should read --so as to have--; and
    Line 42, "than would" should read --than would be--.

<u>COLUMN 10:</u>

Line 8, "employing an the" should read --employing an--.